(12) United States Patent
Field et al.

(10) Patent No.: US 8,579,848 B2
(45) Date of Patent: Nov. 12, 2013

(54) ACTIVE DRAINAGE SYSTEMS WITH PRESSURE-DRIVEN VALVES AND ELECTRONICALLY-DRIVEN PUMP

(75) Inventors: Leslie Field, Portola Valley, CA (US);
Daniel Jenkins, Pomona, CA (US);
Matthew Rickard, Yorba Linda, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/315,329

(22) Filed: Dec. 9, 2011

(65) Prior Publication Data

US 2013/0150774 A1    Jun. 13, 2013

(51) Int. Cl.
*A61M 5/00*    (2006.01)

(52) U.S. Cl.
USPC .................................. 604/9; 606/4; 606/6

(58) Field of Classification Search
USPC ........................ 604/8–10; 606/4–6
See application file for complete search history.

(56) References Cited

U.S. PATENT DOCUMENTS

| | | |
|---|---|---|
| 4,089,329 A | 5/1978 | Couvillon et al. |
| 4,206,762 A | 6/1980 | Cosman |
| 4,457,757 A | 7/1984 | Molteno |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters et al. |
| 5,005,577 A | 4/1991 | Frenkel |
| 5,083,742 A | 1/1992 | Wylie et al. |
| 5,178,604 A | 1/1993 | Baerveldt |
| 5,179,953 A | 1/1993 | Kursar |
| 5,397,300 A | 3/1995 | Baerveldt |
| 5,466,233 A | 11/1995 | Weiner et al. |
| 5,476,445 A | 12/1995 | Baerveldt |
| 5,558,629 A | 9/1996 | Baerveldt |
| 5,707,643 A | 1/1998 | Ogura et al. |
| 5,910,110 A | 6/1999 | Bastable |
| 6,007,511 A | 12/1999 | Prywes |
| 6,048,328 A | 4/2000 | Haller et al. |

(Continued)

FOREIGN PATENT DOCUMENTS

| | | |
|---|---|---|
| DE | 4438201 | 5/1996 |
| EP | 2427097 | 3/2012 |

(Continued)

OTHER PUBLICATIONS

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

(Continued)

*Primary Examiner* — Melanie Hand
(74) *Attorney, Agent, or Firm* — Kenneth D. Bassinger

(57) ABSTRACT

An IOP control system for implantation in an eye of a patient is disclosed. The IOP control system includes a drainage tube configured to convey aqueous humor from an anterior chamber of an eye and includes a pressure-driven valve system in fluid communication with the drainage tube and configured to control flow rates of the aqueous humor. The valve system includes a plurality of pressure-driven valves arranged to operate in cooperation with each other. The IOP control system may include an electronic pump system to further regulate flow.

25 Claims, 5 Drawing Sheets

(56) References Cited

U.S. PATENT DOCUMENTS

| | | |
|---|---|---|
| 6,251,090 B1 | 6/2001 | Avery et al. |
| 6,447,449 B1 | 9/2002 | Fleischman et al. |
| 6,468,283 B1 | 10/2002 | Richter et al. |
| 6,579,235 B1 | 6/2003 | Abita et al. |
| 6,589,198 B1 | 7/2003 | Soltanpour et al. |
| 6,682,500 B2 | 1/2004 | Soltanpour et al. |
| 6,712,764 B2 | 3/2004 | Jeffries et al. |
| 6,719,750 B2 | 4/2004 | Varner et al. |
| 6,749,568 B2 | 6/2004 | Fleischman et al. |
| 6,939,299 B1 | 9/2005 | Petersen et al. |
| 6,976,982 B2 | 12/2005 | Santini et al. |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,354,416 B2 | 4/2008 | Quiroz-Mercado et al. |
| 7,409,863 B2 | 8/2008 | Bateman et al. |
| 7,612,328 B2 | 11/2009 | Kaiser |
| 7,756,559 B2 | 7/2010 | Abreu |
| 8,182,435 B2 | 5/2012 | Dacquay et al. |
| 8,257,295 B2 | 9/2012 | Rickard et al. |
| 8,419,673 B2 | 4/2013 | Rickard |
| 2001/0000527 A1 | 4/2001 | Yaron et al. |
| 2002/0019607 A1 | 2/2002 | Bui |
| 2002/0049374 A1 | 4/2002 | Abreu |
| 2002/0099359 A1 | 7/2002 | Santini, Jr. et al. |
| 2002/0139947 A1 | 10/2002 | Wang |
| 2002/0143284 A1 | 10/2002 | Tu et al. |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0225318 A1 | 12/2003 | Montegrande et al. |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado |
| 2005/0049578 A1 | 3/2005 | Tu et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0131350 A1 | 6/2006 | Schechter et al. |
| 2007/0019156 A1 | 1/2007 | Fink |
| 2007/0032757 A1 | 2/2007 | Medow |
| 2007/0077270 A1 | 4/2007 | Wen |
| 2007/0106199 A1 | 5/2007 | Krivoy et al. |
| 2007/0109117 A1 | 5/2007 | Heitzmann et al. |
| 2007/0123767 A1 | 5/2007 | Montegrande et al. |
| 2007/0129623 A1 | 6/2007 | Fleischmann et al. |
| 2007/0212397 A1 | 9/2007 | Roth |
| 2008/0015421 A1 | 1/2008 | Penner |
| 2008/0027478 A1* | 1/2008 | Connors et al. ............... 606/192 |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2009/0069648 A1 | 3/2009 | Irazqui et al. |
| 2009/0076367 A1 | 3/2009 | Sit et al. |
| 2009/0143713 A1 | 6/2009 | Dam et al. |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0121348 A1 | 5/2010 | Van Der Burg et al. |
| 2010/0174272 A1 | 7/2010 | Weiner |
| 2010/0222769 A1 | 9/2010 | Meng et al. |
| 2010/0234717 A1 | 9/2010 | Wismer |
| 2010/0253167 A1 | 10/2010 | Charnley et al. |
| 2010/0305550 A1 | 12/2010 | Meng et al. |
| 2011/0046536 A1 | 2/2011 | Stegman et al. |
| 2011/0071454 A1 | 3/2011 | Dos Santos |
| 2011/0071456 A1 | 3/2011 | Rickard |
| 2011/0071505 A1 | 3/2011 | Rickard et al. |
| 2011/0248671 A1 | 10/2011 | Dos Santos |

FOREIGN PATENT DOCUMENTS

| | | |
|---|---|---|
| WO | WO 93/03665 | 3/1993 |
| WO | 9803809 | 1/1998 |
| WO | WO 98/03665 | 1/1998 |
| WO | 9938470 | 8/1999 |
| WO | WO 01/94784 | 12/2001 |
| WO | 02056758 | 7/2002 |
| WO | WO 03/001991 | 1/2003 |
| WO | WO 03/102632 | 12/2003 |
| WO | 2005088417 | 9/2005 |
| WO | 2007127305 A2 | 11/2007 |
| WO | WO 2007/136993 | 11/2007 |
| WO | 2008061043 | 5/2008 |
| WO | 2008084350 | 7/2008 |
| WO | 2009010799 | 1/2009 |
| WO | WO 2009/026499 | 2/2009 |
| WO | WO 2009/049686 | 4/2009 |
| WO | WO 2009/081031 | 7/2009 |
| WO | 2010129446 | 11/2010 |
| WO | 2011034727 | 3/2011 |
| WO | 2011034738 | 3/2011 |
| WO | 2011034740 | 3/2011 |
| WO | 2011034742 A2 | 3/2011 |
| WO | 2011035218 | 3/2011 |
| WO | 2012012017 | 1/2012 |

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466-469, Lyon, France.

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/049424, Nov. 26, 2010, 15 pages.

International Searching Authority, Search Report of the International Searching Authority, PCT/US2011/036742, Aug. 17, 2011, 2 pages.

Lam, Andrew K.C. and Douthwaite, William A., "The Effect of an Artificially Elevated Intraocular Pressure on the Central Corneal Curvature," Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

(56) References Cited

OTHER PUBLICATIONS

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Puers, Robert, "Linking Sensors with Telemetry: Impact on the System Design," in Proc. 8th Int'l Conference of Solid State Sensors, Actuators, Eurosens, Jun. 25-29, 1995, pp. 169-174, Stockholm, Sweden.

Schnakenberg, U., et al, "Initial Investigations on Systems for Measuring Intraocular Pressure," Sensors and Actuators, 2000, p. 287-291, vol. 85, Elsevier Science B.V., Germany.

Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.

Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-$\gamma$; pp. 335-336; Subject Collection Medicine."

International Searching Authority, Invitation to Pay Additional Fees and, Where Applicable, Protest Fee (Partial Search Report attached), PCT/US2012/067741, Apr. 2, 2013, 6 pages.

Neagu Cristina R.; "A Medical Microactuator Based on an Electrochemical Principle"; Thesis at the Twente University,the Netherlands, Enschede; Aug. 28, 1998; pp. 1-162.

Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; Trans Am Ophthalmol Soc 2009; 107; pp. 60-71.

Erik Stemme and Goran Stemme; "A Valveless Diffuser/Nozzle-Based Fluid Pump"; ScienceDirect; Sensors and Actuators A, 39 (1993); pp. 159-167.

Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.

International Search Report and Written Opinion corresponding to PCT/US2010/047605 dated Dec. 16, 2010.

International Search Report and Written Opinion corresponding to PCT/US2010/047612 dated Dec. 21, 2010.

Driot et al.; "Ocular pharmacokinetics of fluocinolone acetonide after RetisertTM intravitreal implantation in rabbits over a 1-year period"; J. Ocular Pharm; vol. 20; No. 3; pp. 269-275 (2004).

Glybina et al.; "Neuroprotective properties of fluocinolone acetonide chronically delivered into the vitreous of albino RCS rats"; IVOS; vol. 47; ARVO E-Abstract 1028 (2006).

Kupperman et al.; "Efficacy and safety of a novel intravitreous dexamethasone drug-delivery system after applicator or incisional placement in patients with macular edema"; IVOS; vol. 47; ARVO E-Abstract 5913 (2006).

Miyamoto et al.; "Biodegradable scleral implant for intravitreal controlled release of fluconazole"; Current Eye Res.; vol. 16; No. 19; pp. 930-935 (1997).

Miruthyunjaya et al.; "An intravitreal sustained release fluocinolone acetonide device to treat severe experimental uveitis"; IVOS; vol. 44; ARVO E-Abstract 4215 (2003).

Ratanapakorin et al.; "Helical intravitreal triamcinolone implant: An explanation survival study"; IVOS; vol. 46; ARVO E-Abstract 484 (2005).

Rego et al; "In vitro evaluation of sustained-release intravitreal dexamethasone implants"; IVOS; vol. 45; ARVO E-Abstract 5060 (2004).

Sakurai et al.; "Scleral plug of biodegradable polymers containing ganciclovir for experimental cytomegalovirus retinitis"; IVOS; vol. 42; No. 9; pp. 2043-2048 (2004).

See et al.; "Safety and drug release profile of injectable intravitreal sustained-release fluocinolone acetonide device"; IVOS; vol. 47; ARVO E-Abstract 5119 (2006).

Tano et al.; "Helical intravitreal implant: surgical method development and outcomes"; IVOS; vol. 46; ARVO E-Abstract 483 (2005).

Varner et al.; "Development of a minimally invasive intravitreal implant for drug delivery"; IVOS; vol. 44; ARVO E-Abstract 4214 (2003).

Weiner; "Drug delivery systems in ophthalmic applications; In Ocular Therapeutics; Eye on New Discoveries; T. Yorio, A. Clark, M. Wax, Eds, Elsevier Press/Academic Press, New York", pp. 7-43 (2007).

Yasukawa et al.; "Biodegradable scleral plugs for vitreoretinal drug delivery"; Adv. Drug Del. Rev.; vol. 52; No. 1; pp. 25-36 (2001).

International Search Report and Written Opinion corresponding to PCT/US2012/068878 dated Apr. 3, 2013.

International Search Report and Written Opinion corresponding to PCT/US2012/067747 dated Apr. 2, 2013.

\* cited by examiner

ACTIVE DRAINAGE SYSTEMS WITH PRESSURE-DRIVEN VALVES AND ELECTRONICALLY-DRIVEN PUMP

BACKGROUND

The present disclosure relates generally to valves and associated systems and methods for use in ophthalmic treatments. In some instances, embodiments of the present disclosure are configured to be part of an IOP control system.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. These devices are generally passive devices and do not provide a smart, interactive control of the amount of flow through the drainage tube. In addition, fluid filled blebs frequently develop at the drainage site. The development of the bleb typically includes fibrosis, which leads to increased flow resistance and it is generally the case that this resistance increases overtime. This development and progression of fibrosis reduces or eliminates flow from the anterior chamber, eliminating the capacity of the drainage device to affect IOP.

In an ideal scenario, bleb sizes are limited and bleb fluid is gradually absorbed into the body at a rate that matches or exceeds the drainage rate, thereby keeping the bleb size small. However, when drainage flow rates exceed the rate of absorption into the body, the bleb size and pressure may increase. Too much pressure can cause a bleb to migrate to an undesirable location or can lead to fibrosis. Fibrosis may include generation of at least some scar tissue, reducing the ability of the eye to reabsorb fluid in the location of the bleb. As the bleb continues to grow, the risk of leakage may increase, along with the effects of fibrosis. Fibrosis may also cause an increase in resistance at the drainage site of the implant and/or cause the lumens of passive implants to clog over time, causing the IOP to rise.

Furthermore, as bleb sizes increase, and the body, due to fibrosis or other conditions, cannot reabsorb the bleb fluid, bleb pressure may match the interior chamber eye pressure, reducing or eliminating flow from the interior chamber, and thereby eliminating the capacity of the drainage device to affect IOP pressure. Therefore, the performance of these passive drainage implants is often dictated by the patient's fibrotic response to the implant.

Accordingly, there exists a need for an IOP control system or implant that protects against under-filtration while simultaneously guarding against over-filtration, and consequently reduces or eliminates bleb formation and fibrotic changes. The system and methods disclosed herein overcome one or more of the deficiencies of the prior art.

SUMMARY

This disclosure relates generally to implantable systems for controlling intraocular pressure (IOP).

In one exemplary embodiment, an IOP control system for implantation in an eye of a patient comprises a drainage tube and a pressure-driven valve system. The drainage tube may be configured to convey aqueous humor from an anterior chamber of the eye. The pressure-driven valve system may be in fluid communication with the drainage tube. The valve system may be actuatable in response to pressure differentials and may be configured to control flow rates of the aqueous humor. The valve system may include a first pressure-driven valve and a second valve, wherein the pressure-driven valve system is configured to control flow rates of the aqueous humor along the drainage tube by shifting in response to pressure differentials between the anterior chamber of the eye, the drainage site, and the atmospheric pressure acting on the pressure-driven valves.

In another exemplary embodiment, an IOP control system for implantation in an eye of a patient may comprise a drainage tube, a pressure-driven valve system, and an electrically-driven pump system. The drainage tube may be configured to convey aqueous humor from an anterior chamber of the eye. The pressure-driven valve system may be in fluid communication with the drainage tube, and the valve system may be actuatable in response to pressure differentials acting on the pressure-driven valves and configured to control flow rates of the aqueous humor. The electrically-driven pump system may be in fluid communication with the drainage tube and the pressure-driven valve system, and the electrically-driven pump system may be arranged to selectively control aqueous humor flow rates through the drainage tube and influence the pressure differentials affecting the valve system.

In another exemplary embodiment, an TOP control system for implantation in an eye of a patient may comprise a drainage tube, a pressure-driven valve system, and an electrically-driven pump system. The drainage tube may be configured to convey aqueous humor from an anterior chamber of the eye. The pressure-driven valve system may be in fluid communication with the drainage tube, and include a first pressure-driven valve and a second pressure-driven valve arranged in series to operate independently of each other. The pressure driven valves may each include a flow control member configured to control flow rates of the aqueous humor along the drainage tube by shifting in response to pressure differentials between the anterior chamber of the eye, the drainage site, and the atmospheric pressure. The electrically-driven pump system may be in fluid communication with the drainage tube and the pressure-driven valve system. The electrically-driven pump system may be configured to selectively control aqueous humor flow rates through the drainage tube and influence the pressure differentials affecting the valve system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 5a illustrates a scenario where a first valve is open and a second valve is closed. FIG. 5b illustrates a scenario where both valves are open.

DETAILED DESCRIPTION OF THE PREFERRED EMBODIMENTS

Figure 1:
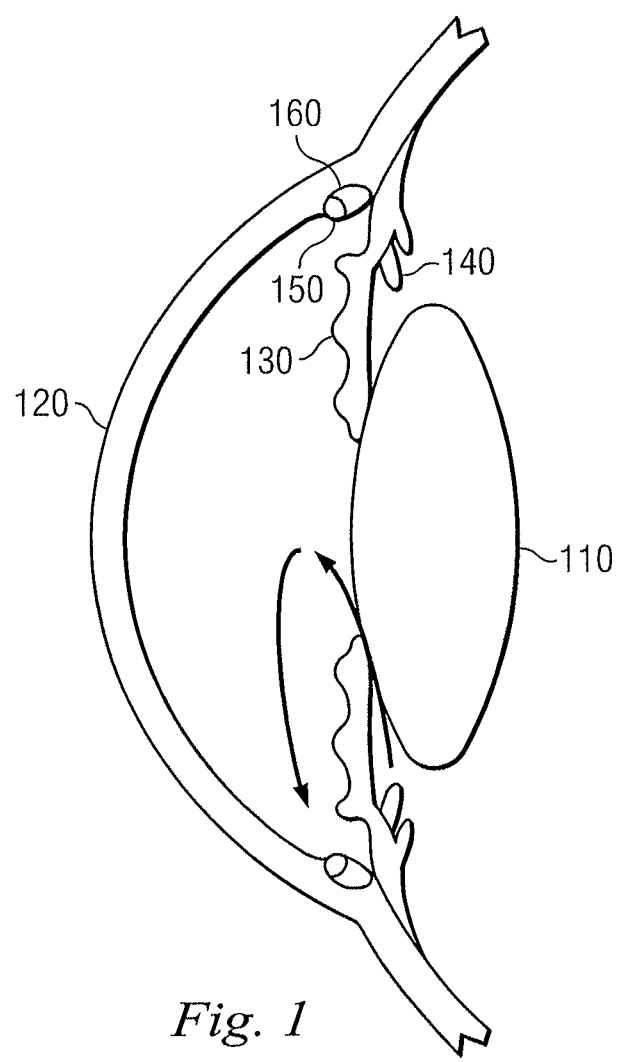
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

Figure 2:
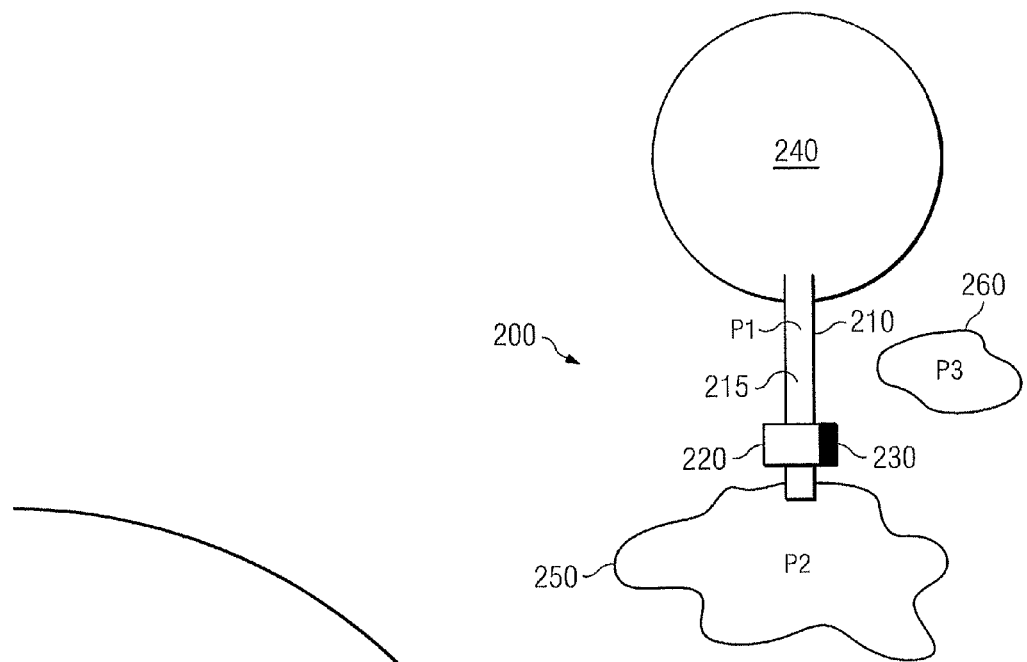
FIG. 2 is a schematic diagram of an IOP control system according to one embodiment of the present disclosure.

FIG. 2 is a diagram of an exemplary IOP control system 200, including a drainage tube 210, a valve system 220, and a divider 230. In the embodiment pictured in FIG. 2, the IOP sensor system 200 is arranged in the eye such that three areas of pressure interact with the IOP sensor system 200: P1, P2, and P3. Pressure area P1 reflects the pressure of the anterior chamber 240, pressure area P2 reflects the pressure of a drainage site in the subconjunctival space (and may reflect bleb pressure), and pressure area P3 reflects a pressure located remotely from P1 and P2 (effectively reflecting atmospheric pressure). In some embodiments, pressure area P1 reflects the pressure located in a lumen or tube that is in fluidic communication with the anterior chamber 240.

The drainage tube 210 drains aqueous humor from the anterior chamber 240 of the eye. The valve system 220 controls the flow of aqueous humor through the lumen 215 of the tube 210. In the embodiment shown, the pressure area P1 reflects the pressure in the lumen 215 upstream from the valve system 220 and downstream from the anterior chamber 240. In this manner, pressure area P1 reflects the pressure in the anterior chamber 240. The expected discrepancy between the true anterior chamber pressure and that reflected by area P1 when located in a tube downstream of the anterior chamber 240 (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

In some embodiments, a divider 230 separates pressure areas P1 and P2 from pressure area P3. Pressure area P2 reflects the pressure at a drainage site, in FIGS. 2 and 3. As such, pressure area P2 may be located in a pocket, such as a bleb, that generally contains aqueous humor or in communication with such a pocket, via a tube, for example, and is in a wet location. Pressure area P3 is physically separated from both pressure area P1 and pressure area P2 by divider 230. Divider 230 is a physical structure that separates and isolates the pressure area P1 and the wet drainage site 250 of pressure area P2 from the (relatively) dry location 260 of pressure area P3. In some embodiments, the divider 230 includes the physical components of the valve system 220, such as parts of a housing. Note that the divider 230 may take many forms, such as, but not limited to a tube fluidically coupling pressure area P3 to a remote site or a pocket away from and fluidically independent of the drainage site.

In some embodiments of the present disclosure, the atmospheric pressure area P3 reflects the pressure in an area in close proximity to the eye, and in one embodiment, the pressure area P3 may reflect the pressure in the eye under the conjunctiva. In such cases, pressure area P3 reflects a pressure that can be correlated with atmospheric pressure. Pressure area P3 may also reflect the pressure of a (relatively) dry portion 260 of the subconjunctival space, separate and apart from the drainage site 250. Regardless of location, pressure area P3 is intended to reflect atmospheric pressure in the vicinity of the eye or at the eye's surface.

Generally, IOP is a gauge pressure reading—the difference between the absolute pressure in the eye (as reflected by P1) and atmospheric pressure (as reflected by P3). Atmospheric pressure, typically about 760 mm Hg, often varies in magnitude by 10 mmHg or more depending on weather conditions or indoor climate control systems. In addition, the effective atmospheric pressure can vary significantly—in excess of 100 mmHg—if a patient goes swimming, hiking, riding in an airplane, etc. Such a variation in atmospheric pressure is significant since IOP is typically in the range of about 15 mm Hg. Thus, for accurate control of IOP, it is desirable to have an IOP control system reactive to the pressure differential across the pressure of the anterior chamber (as reflected by P1) and atmospheric pressure in the vicinity of the eye (as reflected by sensor P3). Therefore, in one embodiment of the present disclosure, the IOP control system 200 reacts to the pressure differential across P1 and P3 continuously or nearly continuously so that the actual IOP (as P1-P3 or P1-f(P3)) can be responded to accordingly.

Figure 3:
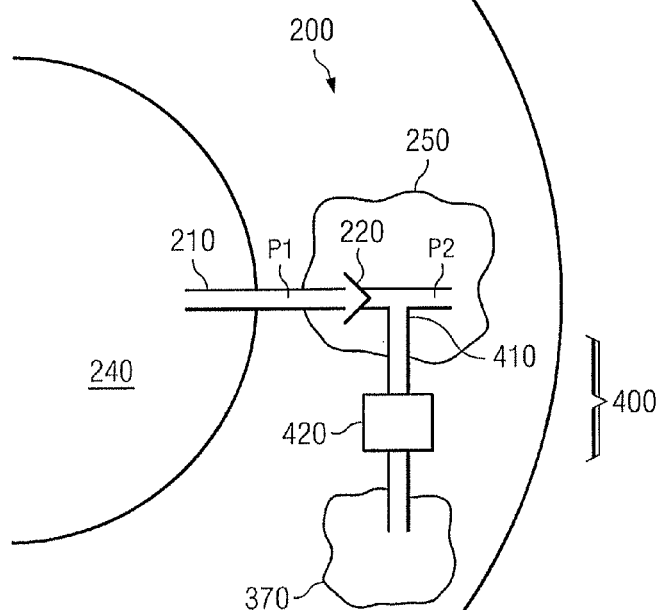
FIG. 3 is a schematic diagram of one possible application of an IOP control system according to one embodiment of the present disclosure.

FIG. 3 is a diagram of one possible application of the IOP control system 200, shown implanted in the eye. In FIG. 3, pressure area P1 reflects the pressure in the anterior chamber 240 of the eye. Pressure area P2 reflects the pressure at a drainage site 250. The drainage tube 210 may be arranged to shunt fluid from the anterior chamber 240 to the drainage site 250, which may be at any of numerous locations within the eye. For example, some tubes 210 are arranged to shunt aqueous from the anterior chamber 240 to the subconjunctival space, thus forming a bleb under the conjunctiva, or, alternatively, to the subscleral space, thus forming a bleb under the sclera. Other tube designs shunt aqueous humor from the anterior chamber to the suprachoroidal space, the supraciliary space, the juxta-uveal space, or to the choroid, thus forming blebs in those respective locations. In other applications, the drainage tube 210 shunts aqueous humor from the anterior chamber 240 to Schlemm's canal, a collector channel in Schlemm's canal, or any of a number of different blood vessels like an episcleral vein. In some examples, the drainage tube 210 even shunts aqueous humor from the anterior chamber 240 to outside the conjunctiva. Each of these different anatomical locations to which aqueous humor is shunted is an example of a drainage site 250. Other examples of a drainage site 250 include, but are not limited to: a subconjunctival space, a suprachoroidal space, a subscleral space, a supraciliary space, Schlemm's canal, a collector channel, an episcleral vein, a uveo-scleral pathway, and other locations.

FIG. 3 illustrates the IOP control system 200 positioned in the eye with one end of the drainage tube 210 located in the anterior chamber 240 and the opposite end located outside the anterior chamber 240 in the drainage site 250. Typically, one end of the tube 210 resides in the anterior chamber 240 and the other end of the tube 210 resides in the subconjunctival space. In other embodiments, the other end of the tube may reside inside Schlemm's canal to allow the aqueous humor to exit the eye through the connector channels and the episcleral veins. It may reside, for example, in any of the locations set forth above. The IOP control system 200 may be positioned within the eye in the subconjunctival pocket between the conjunctiva and the sclera with the anterior border of the IOP control system 200 positioned slightly posterior to the limbus (the border between the cornea and the sclera). The IOP control system 200 may be held in place within the eye via anchoring structures, the angle of implantation and surrounding anatomy, or by a spring force or other mechanisms that stabilize the IOP control system 200.

The valve system 220 is connected to the drainage tube 210 and controls the flow of aqueous humor through the lumen of the tube 210 from the anterior chamber 240 to the drainage site 250. As indicated above, pressure area P1 reflects the pressure of the anterior chamber or an area in fluid communication with the anterior chamber, and therefore, as shown in the embodiments of FIGS. 2 and 3, pressure area P1 is located upstream from valve system 220. In FIG. 3, pressure area P1 is located in the subconjunctival space but is in fluid communication with the anterior chamber 240. Because there is almost no pressure difference between the anterior chamber 240 and the interior of the tube 210 that is in fluid contact with the anterior chamber 240, pressure area P1 effectively reflects the pressure of the anterior chamber 240.

Given that pressure area P1 reflects the pressure in the anterior chamber 240 and pressure area P2 reflects pressure at the drainage site 250, the difference in pressure between the two pressure areas (P1-P2) provides an indication of the pressure differential between the anterior chamber 240 and the drainage site 250. Because the pressure area P3 reflects atmospheric pressure, the difference in pressure between the pressure areas P1 and P3 provides an indication of IOP (the pressure differential between the anterior chamber 240 and the atmospheric pressure). Similarly, the difference in pressure between the pressure areas P2 and P3 provides an indication of the pressure differential between the pressure at the drainage site 250 and atmospheric pressure. The IOP control system responds to the pressure differentials between P1, P2, and P3 to control the valve system 220 and thereby control the flow rate of aqueous humor through drainage tube 210. More specifically, the various pressure differentials across pressure areas P1, P2, and P3 (P1-P2, P1-P3, P2-P3) drive the valve system 220 and dictate the flow rate of aqueous humor through the drainage tube 210 without requiring external power at the valve system 220.

While several complications may arise from elevated IOP, various complications may arise from excessively low IOP as well. For example, hypotony is a complication associated with surgeries that serve to shunt the aqueous humor from the anterior chamber 240 to a drainage site 250. Hypotony is a dangerous, rapid drop in IOP that can result in severe consequences, such as choroidal hemorrhage and choroidal detachment. Thus, it is desirable to control the rate of aqueous outflow from the anterior chamber 240 to the drainage site 250 not only to prevent underfiltration of aqueous humor, but also to prevent overfiltration and hypotony. The valve system 220 can respond to the pressure differentials between the pressure areas P1, P2, and P3 to control the flow rate through the drainage tube 210.

In another embodiment of the present disclosure, IOP (based on the pressure differential between pressure areas P1 and P3) can be controlled by the construction of valve system 220. In this manner, IOP is the control parameter. To accomplish this, the valve system 220 can be constructed to have an opening designed to maintain a particular IOP or IOP range. Accordingly, the valve system 220 can control a rapid IOP drop or hypotonous situation, as may occur immediately following surgery. That is, the valve system 220 can be constructed to permit a gradual drop in IOP based on pressure differentials across pressure areas P1 and P3.

In another embodiment of the present disclosure, the pressure differential across pressure areas P2 and P3 can control valve system 220 so as to prevent the formation of a bleb or control the morphology of a bleb. One of the problems associated with implant surgery is bleb failure. A bleb can fail due to poor formation or fibrosis. The pressure in the bleb is one factor that determines bleb morphology. As explained above, too much pressure can cause a bleb to migrate to an undesirable location or can lead to excess fibrosis and underfiltration. The valve system 220 takes into account the pressure area P2 to control the bleb pressure. In one embodiment of the present disclosure, the pressure differential between the bleb (as reflected by P2) and atmospheric pressure (as reflected by P3) can be used to control valve system 220 to optimize the success of the IOP control system and maintain a desirable bleb pressure. In this manner, the IOP control system 200 of the present disclosure can also be used to properly maintain a bleb.

Figure 4:
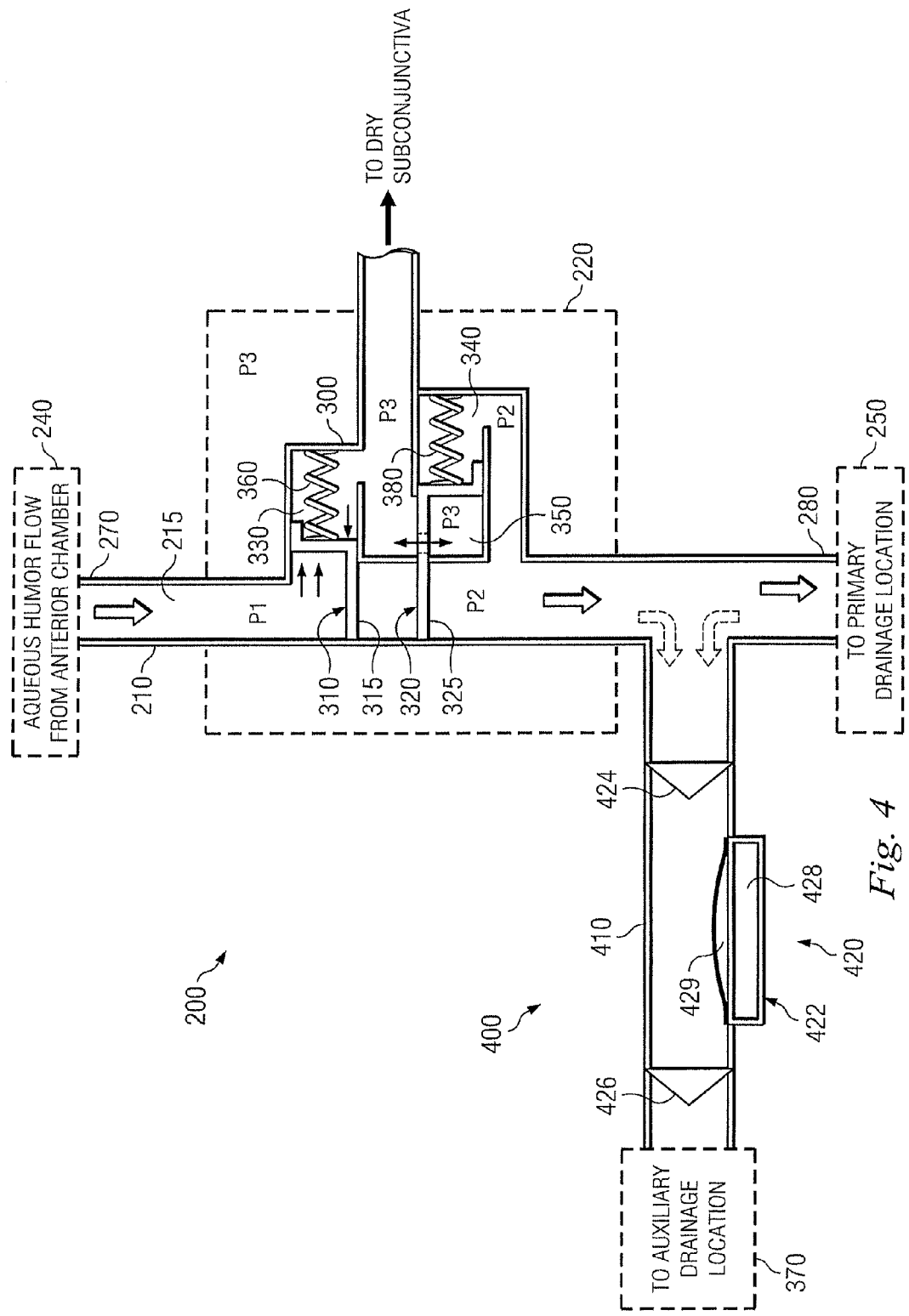
FIG. 4 is a schematic diagram of an IOP control system incorporating a pressure-driven valve system and an electrically-driven pump system according to one embodiment of the present disclosure.

FIG. 4 shows an exemplary embodiment of the IOP control system 200, including the drainage tube 210 and the valve system 220, in greater detail. The valve system 220 is disposed along, and may form a part of, the drainage tube 210 between the tube inlet 270 in the anterior chamber 240 and tube outlet 280 at the drainage site 250. In some embodiments, the valve system 220 is disposed within the lumen 215 of the drainage tube 210 between the tube inlet 270 and the tube outlet 280. The valve system 220 is configured to control the flow of fluid through the drainage tube 210, and thereby control pressure in the eye, including the IOP. For example, when the IOP is high, the valve system 220 may operate to permit increased flow through the drainage tube 210, and when IOP is low, the valve system 220 may operate to decrease the flow through the drainage tube 210. In the embodiment pictured in FIG. 4, the valve system 220 is configured to respond to various pressure differentials (P1-P3 and P2-P3) and control fluid flow to the drainage site 250. If the drainage site 250 is a bleb, this controlled fluid flow through the drainage tube 210 may decrease fibrosis and increase absorption efficiency. To accomplish this, the valve system 220 is continuously responsive to pressure differentials, including pressure differentials across P1 and P3, and across P2 and P3.

In the embodiment shown in FIG. 4, the valve system 220 includes a housing 300, an inlet valve 310, and an outlet valve 320. In this example, both the inlet valve 310 and the outlet valve 320 are pressure-driven valves that do not require external power or feedback from electronic pressure sensors to operate. The valves 310, 320 operate independently, and drainage of the aqueous humor is only realized when both the inlet valve 310 and the outlet valve 320 are at least partially open. The independent operation of the two pressure-driven valves 310, 320 addresses excessive IOP prevention as well as hypotony prevention while simultaneously addressing the efficacy of drainage and bleb morphology. Note that the geometric construction of the valves in this embodiment is only one possible example and serves the purpose of conveying the functional concepts of the present disclosure. Several alternate valve arrangements are possible, including planar, membrane/boss-style valves fabricated using MEMS (Microelectromechanical Systems) techniques, which have the advantage of no surface-to-surface contact or no motion of one surface past another in a manner that might induce surface friction because the valve operation is based on deflecting and/or deforming membranes to open and close flow paths.

The housing 300 is in fluidic communication with the drainage tube 210. In particular, the housing 300 fluidly interfaces with the drainage tube 210 (pressure areas P1 and P2) and also interfaces with the dry subconjunctiva (pressure area P3). As can be seen in FIG. 4, in the example shown, the valves 310, 320 are anchored in the housing 300, which includes a rigid structure with walls on at least three sides. The inlet valve 310 includes a flow control member 315, a biasing member 360, and a first chamber 330. The outlet valve 320 includes a flow control member 325, a biasing member 380, a second chamber 340, and a third chamber 350. The housing 300 is configured to connect with tube 210 such that the flow control members 315, 325 can slidably shift from the lumen 215 of tube 210 into the housing 300, and visa-versa, to at least partially open and close the lumen 215 to the outflow of aqueous humor.

The first chamber 330, the second chamber 340, and the third chamber 350 are separate and distinct areas within the housing 300. The flow control member 315 creates a sealed separation between the first chamber 330 and the lumen 215, and the flow control member 325 divides the second chamber 340 and the third chamber 350. The first chamber 330 and the third chamber 350 are in communication, thereby allowing pressure area P3 to act on both flow control members 315 and 325. Accordingly, as the pressure increases against one side of the flow control member 315 or 325, the pressure increase acts to displace the flow control member in only one direction. The first chamber 330 houses flow control member 315 and conveys the pressure of pressure area P3 on one side of the flow control member 315. The pressure of pressure area P1 is conveyed on the opposite side of the flow control member 315. The second chamber 340 houses the flow control member 325 and conveys the pressure of pressure area P2 on one side of the flow control member 325. The third chamber 350 is formed by the walls of the housing 300 and the flow control member 325 itself, and conveys the pressure of pressure area P3 on the opposite side of the flow control member 325.

The inlet valve 310 is configured to allow or block aqueous humor flowing from the anterior chamber 240 through the drainage tube 210 to the drainage site 250. The inlet valve 310 is configured as a throttle valve that can completely or partially block the flow of aqueous humor by extending the flow control member 315 completely or partially across the lumen 215 of the tube 210. The flow control member 315 is attached to the housing 300 via a biasing member 360. The biasing member 360 assumes a contracted condition when the inlet valve 310 is open or partially open and the flow control member 315 is seated at least partially within the first chamber 330. The biasing member 360 assumes an expanded condition when the inlet valve 310 is closed or partially closed and the flow control member 315 extends across or partially across the lumen 215 of the tube 210. In one example, the biasing member 360 is a spring element used to bias the inlet valve 310 to a partially open condition.

In the present embodiment, the flow control member 315 is an S-shaped member that directs flow by shifting within the lumen 215 of the drainage tube 210 and the housing 300 in response to the pressure differential between the anterior chamber pressure (as reflected by pressure area P1) against one side of the flow control member 315 and the dry subconjunctival pressure (as reflected by pressure area P3, which is expected to correspond to atmospheric pressure) against the opposite side of the flow control member 315. In other embodiments, the S-shaped member is a MEMS component or other element allowing pressure differentials to increase or decrease flows. The inlet valve 310 is open when the IOP (P1-P3) is in excess of the opening pressure of the inlet valve 310 (equivalent to the target IOP), for example 12 mm Hg+/−1 mm Hg, thereby allowing aqueous humor to flow through the drainage tube 210 in the direction of the outlet valve 320. This ensures that drainage of the aqueous humor can occur through the drainage tube 210 if the IOP is elevated. Otherwise, the inlet valve 310 is closed. Therefore, if the IOP (P1-P3) is lower than the opening pressure of the inlet valve 310, then the inlet valve 310 will not open and aqueous humor will not leave the anterior chamber 240 through the IOP control system 200. In addition, the resistance of the biasing member 360 decreases with greater displacement (that is, resistance of biasing member 360 decreases as inlet valve 310 is more closed). Accordingly, in higher pressure situations, the valve 310 will assume a more open condition than in lower pressure situations.

The outlet valve 320 is configured to permit or block the exit of aqueous humor from the valve system 220 for release at the drainage site 250 or, in some embodiments, for further regulation and release at an auxiliary drainage site 370. The outlet valve 320 is configured as a throttle valve that can completely or partially block the flow of aqueous humor by extending the flow control member 325 completely or partially across the lumen 215 of the tube 210. The flow control member 325 is attached to the housing 300 via a biasing member 380. The biasing member 380 assumes a contracted condition when the outlet valve 320 is open or partially open and the flow control member 325 is seated at least partially within the second chamber 340. The biasing member 380 assumes an expanded condition when the outlet valve 320 is closed or partially closed and the flow control member 325 extends across or partially across the lumen 215 of the tube 210. Like the biasing member 360, the biasing member 380 may be a spring element used to bias the valve 320 to a desired position. In some embodiments, the biasing forces of the biasing members 360, 380 are substantially similar, while in other embodiments the biasing forces are different and are selected to achieve desired flow profiles for particular pressure conditions.

The flow control member 325 directs flow by shifting within the lumen 215 of the drainage tube 210 in response to the pressure differential between the wet and dry subconjunctival pressures (as reflected by pressure areas P2 and P3, respectively). The outlet valve 320 opens when the gauge pressure at the drainage site 250 (P2-P3) is below the closing pressure of the outlet valve 320 (equivalent to the maximum design or target pressure of the drainage site), for example 4 mmHg+/−2 mmHg, thereby allowing aqueous humor to flow through the drainage tube 210 in the direction of the drainage site 250 or, in some embodiments, an auxiliary drainage site 370. Therefore, if the gauge pressure at the drainage site 250 (P2-P3) is higher than the closing pressure of the outlet valve 320, then the outlet valve 320 will be closed and the aqueous humor will not leave the eye through the IOP control system 200. In addition, the resistance of the biasing member 380 decreases with greater displacement (that is, resistance of biasing member 380 decreases as outlet valve 320 is more closed). Accordingly, in lower pressure situations (referring again to P2 relative to P3), the valve 320 will assume a more open condition than in high (P2-P3) pressure situations.

FIG. 4 illustrates an under-pressure prevention mechanism of the valve system 220, depicting a situation where both the inlet valve 310 and the outlet valve 320 are closed with the flow control members 315, 325 extending across the lumen 215, thereby blocking the flow of aqueous humor through the drainage tube 210. It is desirable not to allow the IOP to drop below a certain threshold, for example, 6 mmHg. Any intraocular pressure below such a threshold is considered hypotonous pressure and is dangerous to the eye, as explained above. The valve system 220 is self-limiting because the pressure-driven valves 310, 320 will be in an open or mostly open state unless the pressure differential associated with the valve 310 is less than its closing pressure and/or the pressure differential associated with valve 320 is greater than its closing pressures. In the situation depicted in FIG. 4, the inlet valve 310 is closed because the IOP (P1-P3) is below the opening pressure of the inlet valve 310. The outlet valve 320 is closed because the gauge pressure at the drainage site 250 (P2-P3) is at or above the opening pressure of the outlet valve 320. The outlet valve 320 being closed ensures that over-filtration does not occur, which could cause a bleb to over-pressurize and result in possible excess fibrotic resistance.

Figure 5A:
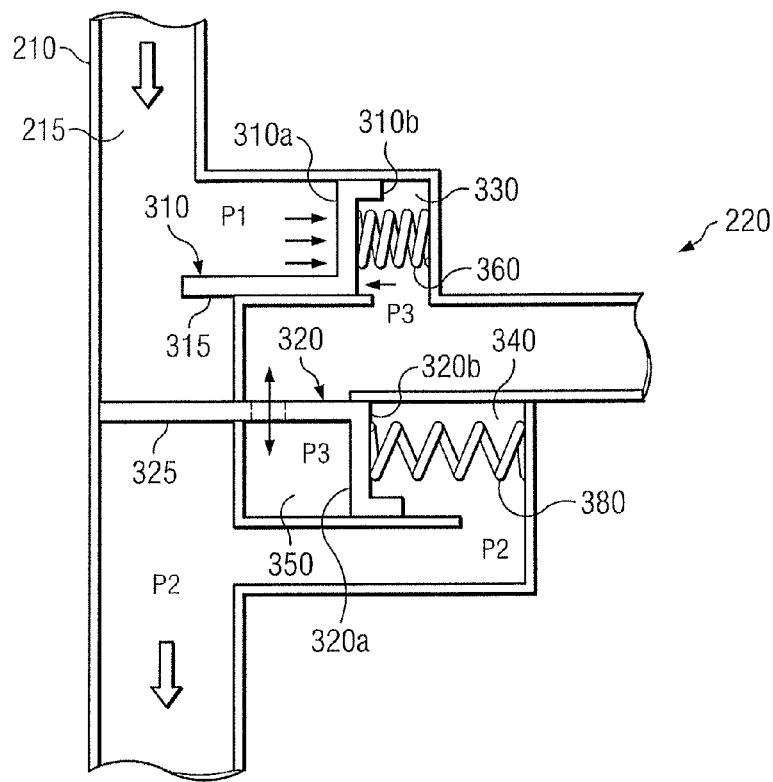
FIGS. 5a and 5b are schematic diagrams of a pressure-driven valve system according to one embodiment of the present disclosure.
Figure 5B:
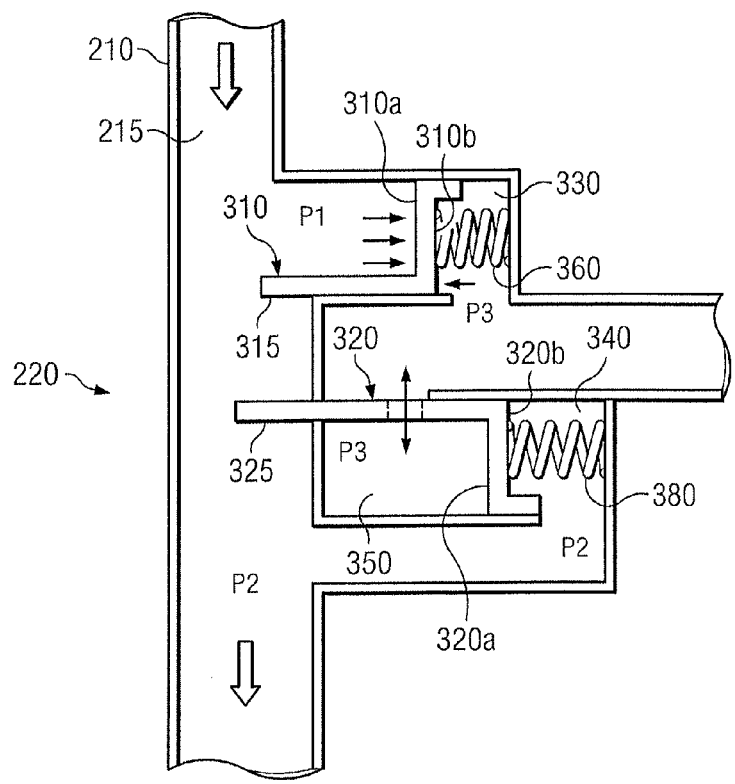

FIGS. 5a and 5b illustrate the valve system 220 in flow-permitting conditions. As described above, the pressure-driven inlet valve 310 responds to changes in IOP (P1-P3) and the pressure-driven outlet valve 320 responds to changes in gauge pressure at the drainage site (P2-P3).

FIG. 5a illustrates the valve positions when the IOP and the drainage site pressure both exceed desired values, depicting a situation where the inlet valve 310 is open and the outlet valve 320 is closed. This over-pressure prevention configuration of the valve system 220 ensures that drainage of the aqueous humor can occur through the drainage tube 210 if the IOP is elevated. The flow control member 315 allows flow through the tube 210 by shifting out of the lumen 215 of the drainage tube 210 and into the housing 300 in response to the pressure differential between the anterior chamber pressure (as reflected by pressure area P1) against one side 310a of the flow control member 315 and the dry subconjunctival pressure (as reflected by pressure area P3, which is expected to correspond to atmospheric pressure) against the opposite side 310b of the flow control member 315. The shifting of the flow control member 315 into the housing 300 serves to push the biasing member 360 into a contracted condition and compact the volume of the first chamber 330. The size of the opposing sides 310a, 310b of the flow control member 315 and the compression force of the biasing member 360 dictate the pressure differential required to open the inlet valve 310. In one example, these are selected so that the inlet valve 310 remains closed when the IOP is below a preset threshold, referred to herein as the opening pressure. Accordingly, when the IOP is below the threshold, the inlet valve 310 remains closed. However, the inlet valve 310 opens when the IOP (P1-P3) is in excess of the opening pressure of the inlet valve 310 (equivalent to the target IOP), thereby allowing aqueous humor to flow through the drainage tube 210 in the direction of the outlet valve 320. In particular, if the intraocular pressure exceeds the opening pressure of the inlet valve 310, then the flow control member 315 will assume an open condition and allow free flow to regulate the IOP down to the desirable range. For example, in the event valve 310 is open, indicating IOP is too high, yet valve 320 is closed because P2-P3 is too high, then the pump serves to create a low pressure at P2 while maintaining a high pressure at auxiliary drainage site 370—thereby allowing valve 320 to open and flow to be realized out of anterior chamber 240.

The outlet valve 320 is closed in FIG. 5a because the pressure at the drainage site 250 (P2) that is conveyed against one side 320b of the flow control member 325 is above the atmospheric pressure of the third chamber (P3) that is conveyed against the opposite side 320a of the flow control member 325. The valve 320 reduces flow through the tube 210 when the pressure in the second chamber 340 displaces the flow control member 325 into the lumen 215 of the drainage tube 210 and expands the volume of the second chamber 340 while simultaneously decreasing the volume of the third chamber 350. Again, as explained above, the size of the opposing sides 320a, 320b of the flow control member 325 and the compression force of the biasing member 380 dictate the pressure differential required to open the outlet valve 320. In one example, these are selected so that the outlet valve 320 remains closed when the drainage site pressure is above a preset threshold, referred to herein as the closing pressure. Accordingly, when the drainage site pressure is above the threshold, the outlet valve 320 remains closed. The outlet valve 320 being closed ensures that over-filtration does not occur into a drainage site 250 that may already possess an elevated pressure. This over-pressure prevention configuration of the valve system 210 guards against bleb enlargement and over-pressurization at the drainage site 250.

FIG. 5b illustrates over-pressure and under-pressure prevention configurations of the valve system 210, depicting a situation where both the flow control member 315 and the flow control member 325 are in an open condition. The flow control member 315 allows flow through the tube 210 by shifting out of the lumen 215 of the drainage tube 210 and into the housing 300 in response to the pressure differential between the anterior chamber pressure (as reflected by pressure area P1) against one side 310a of the flow control member 315 and the dry subconjunctival pressure (as reflected by pressure area P3, which is expected to correspond to atmospheric pressure) against the opposite side 310b of the flow control member 315. The shifting of the flow control member 315 into the housing 300 compresses the biasing member 360 into a contracted condition and decreases the volume of the first chamber 330. The inlet valve 310 opens when the IOP (P1-P3) is in excess of the opening pressure of the inlet valve 310 (equivalent to the target IOP), thereby allowing aqueous humor to flow through the drainage tube 210 in the direction of the outlet valve 320. This over-pressure prevention configuration of the valve system 210 ensures that drainage of the aqueous humor can occur through the drainage tube 210 if the IOP is elevated.

The outlet valve 320 is open in FIG. 5b because the pressure difference between the pressure at the drainage site 250 (P2) that is conveyed against one side 320b of the flow control member 325 and the atmospheric pressure of the third chamber (P3) that is conveyed against the opposite side 320a of the flow control member 325 is below the design threshold. The shifting of the flow control member 325 into the housing 300 compresses the biasing member 380 into a contracted condition and decreases the volume of the second chamber 340 while simultaneously increasing the volume of the third chamber 350. The outlet valve 320 being open ensures that drainage of the aqueous humor can occur through the drainage tube 210 if the IOP is elevated.

Though the pressure-driven valves 310, 320 are depicted as comprising S-shaped flow control members 315, 325 attached to compressible members 360, 380 in FIG. 4, the valves can be comprised of any of a number of different flow control structures that meter, restrict, or permit the flow of aqueous humor from the anterior chamber 240 to the drainage site 250. For example, in another embodiment planar, membrane/boss-style valves fabricated using MEMS (Microelectromechanical Systems) techniques are used, which have the advantage of no surface-to-surface motion because the valve operation is based on deflecting and/or deforming membranes to open or close flow paths. In some embodiments, the flow control members of both valves 310, 320 may be in contact with a biocompatible gel to transmit pressure from the aqueous humor at a region of interest. The biocompatible gel may be one of a variety of biocompatible gels, including silicone dielectric gels used with medical grade piezoresistive pressure sensors. These modifications prevent the formation of solid fibers as a result of the proteinaceous content of the aqueous humor, which could mechanically disrupt valve operation. In addition, the valve system 220 may be positioned anywhere in fluid communication with the drainage tube 210, whether within or along the drainage tube 210.

Referring back to FIG. 3, the exemplary IOP control system 200 includes an electric pump system 400. The electric pump system comprises an auxiliary tube 410 and an electric pump mechanism 420. The auxiliary tube 410 and the electric pump mechanism 420 provide an alternative pathway for the outflow of aqueous humor through the valve system 220. The auxiliary drainage tube 410 is fluidly connected to the drainage tube 210. In some embodiments, as in the pictured embodiment, the auxiliary drainage tube 410 runs in a direction substantially perpendicular to the drainage tube 210. The electric pump mechanism 420 works to increase the outflow of aqueous humor and shunt the flow through the auxiliary drainage tube 410 to the auxiliary drainage site 370 when resistance or pressure at the drainage site 250 is so high that desired drainage does not occur and the target IOP cannot be met, most likely due to an enlarged bleb and/or fibrosis at the drainage site 250. For example, in the event valve 310 is open, indicating IOP is too high, yet valve 320 is closed because P2-P3 is too high, then the pump serves to create a low pressure at P2 while maintaining a high pressure at auxiliary drainage site 370—thereby allowing valve 320 to open and flow to be realized out of anterior chamber 240. A number of variations for the layout of the three pressure areas of interest (P2, P3, and the auxiliary drainage site 370) in the IOP control system 200 are contemplated. The auxiliary drainage site 370 may be, for example, a remote location in the subconjunctival pocket either near the drainage site 250 or on a different quadrant of the globe (eye). In some embodiments, the auxiliary drainage site 370 is located 180 degrees from the pressure area P3. For example, the three pressure areas of interest can be located at various locations within the subconjunctival pocket and may occupy various amounts of the implant quadrant.

With reference to FIG. 4, the electric pump mechanism 420 includes a pump 422, a check valve 424, and a check valve 426. The electric pump mechanism 420 is located downstream of the valve system 220 and within the auxiliary drainage tube 410. The electric pump mechanism 420 illustrated in the embodiment pictured in FIG. 4 is located within the auxiliary drainage tube 410 to pump the aqueous humor from the distal portion of the drainage tube 210 into the auxiliary drainage tube 410. The dashed arrows in FIG. 4 indicate the direction of the flow when the pump 422 is activated. It is important to note that operation of the pump mechanism 420 can transport aqueous humor that has collected or pooled in or near the primary drainage site 250 to the auxiliary drainage site 370, thus working to reduce the pressure of pressure area P2 and causing the outlet valve 320 to open.

Figure 7A:
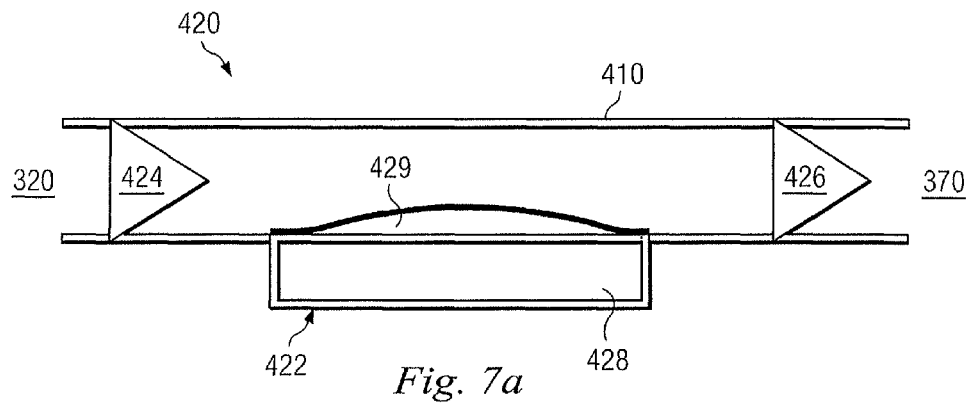
FIGS. 7a and 7b are schematic diagrams illustrating an exemplary pump mechanism according to one embodiment of the present disclosure.
Figure 7B:
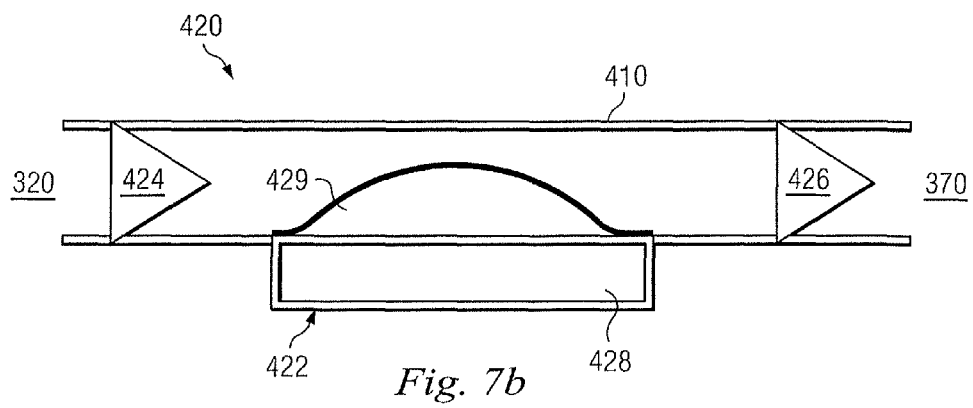

FIGS. 7a and 7b illustrate the pump mechanism 420 and one possible operation of the pump mechanism 420 according to the principles of the present disclosure. The pump 422 comprises a driver 428 and a chamber 429. The check valves 424 and 426 are arranged such that fluid flow is only from the outlet valve 320 to auxiliary drainage site 370. FIG. 7a depicts an off state for the pump 422. In FIG. 7a, the driver 428 keeps the chamber 429 in a low volume configuration. For example, when using electrolysis, the driver 428 does not apply voltage to electrodes in FIG. 7a. In FIG. 7b, the driver 428 causes chamber 429 to expand, thereby decreasing the volume of the auxiliary drainage tube 410. Fluid in the auxiliary drainage tube 410 is directed into auxiliary drainage site 370. For example, when using electrolysis, the driver 428 applies voltage across electrodes to produce gas that expands chamber 429. The driver 428 then allows chamber 429 to return to its low volume state, as illustrated in FIG. 7a. As the volume of chamber 429 decreases, the volume of the auxiliary drainage tube 410 increases, thereby drawing fluid through check valve 424. This fluid can then be directed to the drainage site 410 when the cycle is repeated.

The check valves 424 and 426 may have any desired cracking pressure. One function of the check valves is to ensure that fluid flow is in a direction from the drainage tube 210 to the auxiliary drainage site 370. Any type of check valve or one way valve may be used; for example, a flapper or Reed valve. Alternatively, check valve 434 may include a tapered opening at the pump entrance that decreases in cross-sectional area (according to flow direction) and check valve 426 at pump exit may include a narrow opening that increases in cross-sectional area. Accordingly, because of the shape of the openings, fluid flow will tend to flow easier out the exit port than out the entrance port—even in the absence of any movable parts such as flexing membranes. Additional embodiments may include a one-way check valve such as those described above, in-line between outlet valve 320 and auxiliary drainage site 370, thereby eliminating the chance of fluid flow back toward the interior chamber of the eye.

The driver 428 may be operated to gradually increase the volume of chamber 429 or to rapidly increase the volume of chamber 429. When the driver 428 operates to gradually increase the volume of chamber 429, fluid flow into the auxiliary drainage site 370 can be gradual. When driver 428 operates to rapidly increase the volume of chamber 429, fluid flow into the auxiliary drainage site 370 can be rapid. This rapid movement of fluid can serve to clear blockages in the tubes or the drainage location. When the auxiliary drainage site 370 is a secondary bleb, the rate at which fluid is expelled to the secondary bleb can be controlled to maintain the bleb at a desirable size and/or pressure. In other words, by controlling fluid flow rates to the auxiliary drainage site 370, the drainage site 370 can be maintained in an optimal fashion. For example, a drainage location may only be able to handle a certain volume of fluid in a given time period. The driver 428 may control the volume of chamber 429 such that this volume of fluid does not exceed an acceptable amount in the given time period.

Likewise, the driver 428 may be operated to gradually decrease the volume of chamber 429 or to rapidly decrease the volume of chamber 429. When the driver 428 operates to gradually decrease the volume of chamber 429, fluid flow from the drainage tube 210 (and the outlet valve 320) can be gradual. When driver 428 operates to rapidly decrease the volume of chamber 429, fluid flow from the drainage tube 210 (and the outlet valve 320) can be rapid. This rapid movement of fluid can serve to clear blockages in the tubes leading from the outlet valve 320. Both the speed of the deflection and the overall cycle frequency can be important in driving the flow.

Although the pump mechanism illustrated in FIG. 4 is depicted as an electrochemical pump including check valves, the pump mechanism 420 can be designed based on any of a number of micropump technologies that are suitable for this application. In some embodiments, the pump mechanism 420 can be configured without moving parts (e.g., electroosmotic or electrokinetic). In other embodiments, the pump mechanism 420 can be based on membrane movement driven by other common microelectromechanical system (MEMS) actuation principles (e.g., electrostatic, piezo-excitation, magnetic, thermal, or shape memory alloy). In other examples, the pump mechanism is a scaled down representation of conventional pump, e.g., electromagnetically driven blades. The system design shown in FIG. 4 presents the advantage of an auxiliary flow path for aqueous humor in the branch housing the pump mechanism 420.

Activation of the electric pump mechanism 420 can be based on a number of mechanisms, including, among others: (1) an IOP sensor system 500 comprising one or more electronic pressure sensors that may be located in pressure areas P1, P2, and/or P3 (shown in FIG. 6), (2) a mechanical or electric monitor of the position of the outlet valve 320 or the positions of both the inlet and outlet valves (310 and 320), (3) a pressure-driven mechanism based on the pressure at the pump inlet (equivalent to the pressure of pressure area P2). For example, in one embodiment consistent with mechanism (2), the flow control member 325 of outlet valve 320 and tube 210 comprise an electrical switch such that when outlet valve 320 is fully closed, flow control member 325 physically contacts tube wall 210 and creates an electrical short which can be used as a sensor to indicate that outlet valve 320 is fully closed. Similarly, the flow control member 315 of outlet valve 310 and tube 210 comprise an electrical switch such that when inlet valve 310 is fully closed, flow control member 315 physically contacts tube wall 210 and creates an electrical short which can be used as a sensor to indicate that inlet valve 310 is fully closed. Consistent with this embodiment, the pump mechanism 420 is activated with the signals indicating inlet valve 310 is open and outlet valve 320 is closed.

It is expected that the bleb region of typical IOP control systems, such as Glaucoma Drainage Devices (GDD's), acquires excess fluid in a matter of hours post implantation surgery—even valved GDD's (e.g., the Ahmed Valve) experience this phenomenon because they are based on a P1-P2 logic and cannot differentiate P1-P2 from P1-P3 and/or P2-P3. Though the bleb fills in only a matter of hours, it remains pressurized indefinitely. It is unknown at this time if this excess filtration—because it creates relatively high pressure in the bleb—is necessary for fluid to drain from the bleb region to locations downstream of the subconjunctiva. In the event the pressure is not required, that is, if the bleb pressure is not required for drainage from the bleb (e.g. drainage mechanism is osmotic in nature), then the electric pump 420 is required only when fibrosis at the bleb site 250 yields significant (late-stage) excess resistance. This resistance is likely reduced (or delayed) because some embodiments of the present disclosure reduce the fluid (and associated pressure) residing at the bleb site 250 and—by that reduction of mass— likely reduce the rate of fibrotic growth. In the event that pressure is required at the bleb for further downstream drainage, then the electric pump mechanism 420 will be required more often as it artificially creates the pressure required for further downstream drainage. That is, in the latter scenario, fluid throughput across the fibrosis is not assisted by nonpressure mechanism such as osmosis.

In general, the electric pump 422 is activated when the IOP is high and the inlet valve 310 is open and the outlet valve 320 is closed, a situation caused by increased flow resistance at the drainage site 250. Thus, the electric pump 422 is generally activated only when there exists a need to overcome increased flow resistance at the drainage site 250 and open the valve system 220 to decrease IOP. In some embodiments, the pump 422 is activated while the patient sleeps or is near an external power source; and the pump mechanism is deactivated while the patient is awake or away from an external power source. The infrequent activation of the electric pump 422 allows the IOP control system 200 to generally regulate IOP without using external power by using the pressure-driven valve system 220, thereby creating reduced power requirements for overall IOP control system operation. The reduced overall power requirements for operation of the IOP control system 200 allows for potentially longer lasting power sources and reduces implant maintenance.

FIG. 5a depicts a situation of increased flow resistance at the drainage site 250 and thus a likely scenario for pump mechanism activation. In such a situation, the pressure at pressure area P2 is elevated. Activation and operation of the pump mechanism 420 reduces the pressure at the drainage site 250 (P2) such that the outlet valve 320 is forced to open. The outflow of aqueous humor ideally exits the IOP control system 200 in a direction opposite the anterior chamber 240 and spreads in several directions upon exiting the drainage tubes 210. If the pressure at the drainage site 250 (P2) becomes elevated (due to fibrosis or a need to drain aqueous humor at a higher rate than currently achieved), the pump 422 is activated and drainage is shunted through the auxiliary drainage tube 410 to the auxiliary drainage site 370. With reference to FIGS. 4 and 5b, the operation of the pump mechanism 420 reduces the pressure at the drainage site 250 such that the differential between the pressure (P2) that is conveyed against one side 320b of the valve 320 and the atmospheric pressure of the third chamber (P3) that is conveyed against the opposite side 320a of the valve 320 is below the threshold, and the valve 320 opens to allow outflow of the aqueous humor through the auxiliary tube 410.

It should be noted that some contemplated embodiments do not include the electric pump system 400. In addition, in some embodiments, the electric pump mechanism 420 is disposed within or alongside the drainage tube 210. In some embodiments, the two valves and the pump reside on a single chip composed of micromachined layers; for example, those common to MEMS techniques.

Figure 6:
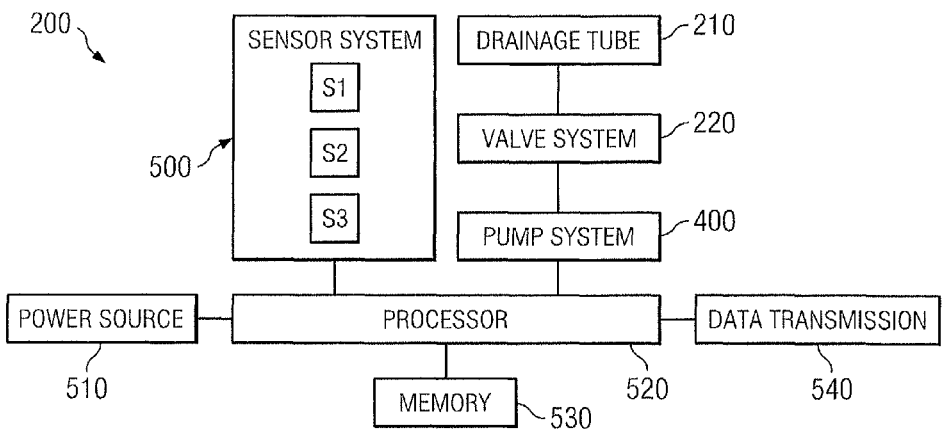
FIG. 6 is a block diagram of an IOP control system according to one embodiment of the present disclosure.

FIG. 6 is a block diagram of an exemplary IOP control system 200 that includes the electronic pump system 400 and is implantable in an eye of a patient according to one embodiment of the present disclosure. The IOP control system 200 is configured in a manner that provides IOP pressure control, but also regulates and controls bleb pressures, reducing complications arising from surgical implant glaucoma treatments. In FIG. 6, the IOP control system 200 includes a power source 510, a pressure sensor system 500, which may include pressure sensors S1, S2, and S3, a processor 520, a memory 530, the valve system 220, and a data transmission module 540.

The power source 510 is typically a rechargeable battery, such as a lithium ion or lithium polymer battery, although other types of batteries may be employed. In addition, any other type of power cell is appropriate for power source 510. Power source 510 provides power to the system 200, and more particularly to the processor 520. The power source 510 can be recharged via inductive coupling such as an RFID link or other type of magnetic coupling. Because the valve system 220 requires no external power, there is a reduced level of required power for overall IOP control system operation. In some examples, sufficient power is provided through on-board batteries or unobtrusive wireless (external) powering. If the power source is unable to provide sufficient energy to power the pump system 400, the IOP control system 200 may operate in a "fall-back" mode wherein the valve system 220 operates to regulate IOP and bleb pressure without the aid of the electric pump 420. Even if the ideal IOP were not achievable in the "fall-back" mode because of excessive pressure at the drainage site 250, the operation of the valve system 220 could provide a significant level of responsive pressure regulation.

The processor 520 is typically an integrated circuit with power, input, and output pins capable of performing logic functions. In some embodiments, the processor 520 is in communication with the sensor system 500, and can receive pressure data from the sensors S1, S2, and/or S3. In various embodiments, processor 520 is a targeted device controller. In such a case, the processor 520 is in communication with and performs specific control functions targeted to a specific device or component, such as a data transmission module 540, power source 510, sensor system 500, valve system 220, pump system 400, or memory 530. For example, the processor 520 can direct or program the pump 420 to function for a period of time even after the outlet valve 320 has opened. In other embodiments, the processor 520 is a microprocessor. In such a case, the processor 520 is programmable so that it can function to control more than one component of the device. In other cases, the processor 520 is not a programmable microprocessor, but instead is a special purpose controller configured to control different components that perform different functions.

In use, some embodiments of the IOP control system 200 may modify the fluid flow rates of aqueous humor to the primary drainage site 250 and the auxiliary drainage site 370. The method begins with the IOP sensor system 500 detecting pressures in pressure areas P1-P3, respectively, and the processor 520 receiving the data from the sensors S1-S3. In some embodiments, the pressure sensor S1 is configured for positioning in fluid communication with the anterior chamber 240 of the eye such that the sensor S1 can measure the pressure of pressure area P1. In some embodiments, the pressure sensor S2 is configured for positioning in fluid communication with the drainage site 250 such that the sensor S2 can measure the pressure of pressure area P2. In some embodiments, the pressure sensor S3 is configured for positioning in fluid communication with the subconjunctival space of the eye such that the sensor S3 can measure the pressure of pressure area P3. In some embodiments, the pressure sensors S1, S2, and S3 are positioned remotely from each other. Based upon algorithms, programs, or coding in the processor or memory, the processor 520 determines whether any flow modifications are required to maintain the IOP or the anterior chamber pressure within a desired target range and whether any modification is required to maintain the bleb pressure within a target range. In some aspects, the processor 520 compares measured pressure data to stored pressure data and determines whether the data is inside or outside acceptable ranges.

For example, in some aspects, determining whether flow modifications are required may include comparing the pressure of the drainage site 250 as measured by sensor S2 to the atmospheric pressure as measured by sensor S3, and determining whether the pump 420 should be activated based on the comparison. In other embodiments, the processor 520 may compare the pressure of the anterior chamber as measured by pressure sensor S1 to either the pressure measured by the sensor S2 or the pressure measured by the sensor S3 to determine whether the pump 420 should be activated based on the comparison. Other examples include other pressure relationships as determined by algorithms to control the pump 420. Although several arrangements are contemplated, in one embodiment, the pressure measurements are weighted in the algorithms or calculation performed by the processor 520 so that the IOP will be decreased if necessary, at the expense of the bleb pressure. In another embodiment, the pressure measurements are weighted in the algorithms or calculation performed by the processor 520 so that the bleb pressure will be decreased if necessary, at the expense of the IOP. If the system determines flow modifications are needed, the processor modifies the flow rates.

The memory 530 is typically a semiconductor memory such as RAM, FRAM, or NAND flash memory. The memory 530 interfaces with processor 520. As such, the processor 520 can write to and read from the memory 530. For example, the processor 520 can be configured to read data from the IOP sensor system 500 and write that data to the memory 530. In this manner, a series of pressure readings can be stored in the memory 530. The processor 520 is also capable of performing other basic memory functions, such as erasing or overwriting the memory 530, detecting when the memory 530 is full, and other common functions associated with managing semiconductor memory.

The data transmission module 540 may employ any of a number of different types of data transmission. For example, the data transmission module 540 may be an active device such as a radio. The data transmission module 540 may also be a passive device such as the antenna on an RFID tag. In this case, an RFID tag includes the memory 530 and the data transmission module 540 in the form of an antenna. An RFID reader can then be placed near the system 200 to write data to or read data from the memory 530. Since the amount of data typically stored in the memory 530 is likely to be small (consisting of IOP readings over a period of time), the speed with which data is transferred is not crucial. Other types of data that can be stored in the memory 530 and transmitted by the data transmission module 540 include, but are not limited to, power source data (e.g. low battery, battery defect), speaker data (warning tones, voices), TOP sensor data (IOP readings, problem conditions), time stamp data, and the like.

Alternatively, the data transmission module 540 may be activated to communicate an elevated IOP condition to a secondary device such as a PDA, cell phone, computer, wrist watch, custom device exclusively for this purpose, remote accessible data storage site (e.g., an internet server, email server, or text message server), or other electronic device. In one embodiment, a personal electronic device uploads the data to the remote accessible data storage site (e.g., an internet server, email server, or text message server). Information may be uploaded to a remote accessible data storage site so that it can be viewed in real time, for example, by medical personnel. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), the processor 520 can read IOP measurements made by an implanted IOP sensor system 500. If the processor 520 reads an unsafe IOP condition, then the data transmission module 540 can alert the patient and medical staff directly or by transmitting the unsafe readings to a secondary device.

Conventional passive check valves in drainage device implants (e.g., the Ahmed Valve) provide a reduced risk of hypotony in the weeks immediately following surgery. But these conventional valves have no mechanism for accounting for drainage site or bleb pressure. The systems disclosed herein may adjust to control flow to the bleb. Accordingly, the systems and methods disclosed herein provide a device that a) requires zero to minimal power (internal or external), and b) presents a mechanism of minimizing bleb height (reducing or eliminating bleb) by controlling the flow through the IOP control system 200 based on pressure differentials (and possibly on detected data from a pressure sensor system 500), which could significantly reduce the effect of fibrosis and also reduce or eliminate other issues related to bleb management.

The systems and methods described herein achieve IOP control with a very small device that utilizes zero to very low power. The system takes into account bleb pressure in regulating drainage flow. Accordingly, based on pressure-driven valves and an optional electronic pump to control the flow rate of aqueous humor, the system provides suitable care for a patient suffering from irregular intraocular pressure.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. An IOP control system for implantation in an eye of a patient, comprising:
   a drainage tube configured to convey aqueous humor from an anterior chamber of the eye;
   a pressure-driven valve system in fluid communication with the drainage tube, the valve system actuatable in response to pressure differentials acting on the pressure-driven valves and configured to control flow rates of the aqueous humor, the pressure-driven valve system comprising a first pressure-driven valve and a second pressure-driven valve arranged in series to operate independently of each other; wherein the pressure-driven valves control flow rates of the aqueous humor along the drainage tube by shifting in response to pressure differentials between the anterior chamber of the eye, the drainage site, and the atmospheric pressure; and further wherein the pressure-driven valves each include an S-shaped flow control member; and
   an electrically-driven pump system in fluid communication with the drainage tube and the pressure-driven valve system, the electrically-driven pump system being arranged to selectively control aqueous humor flow rates through the drainage tube and influence the pressure differentials affecting the valve system.

2. The system of claim 1, wherein the electrically driven pump system is activated to pump aqueous humor from the anterior chamber when the electrically-driven pump system is in the vicinity of an external power source; and the electrically driven pump system is deactivated when the electrically-driven pump system is not in the vicinity of an external power source.

3. The system of claim 1, wherein the pressure-driven valves each include a biasing member connected to the flow control member, the biasing member having an expanded condition and a contracted condition in response to pressure differentials moving the flow control member in a first direction and a second direction opposite the first direction.

4. The system of claim 1, further comprising a processor coupled to the electrically-driven pump system, a pressure sensor system coupled to the processor, and a power source, wherein the processor is configured to control the pump to adjust the rate of aqueous flow through the drainage tube based on sensed pressures.

5. The system of claim 4, wherein the electrically-driven pump system further comprises a memory coupled to the processor, wherein the processor writes values corresponding to sensed pressures to the memory.

6. The system of claim 4, further comprising a data transmission module coupled to the processor.

7. The system of claim 4, wherein the pressure sensor system comprises:
   a first pressure sensor located in fluid communication with the anterior chamber of an eye; and
   a second pressure sensor located at the drainage site;
   wherein a difference between the readings from the first pressure sensor and the second pressure sensor approximates a pressure differential between the anterior chamber and the drainage site.

8. The system of claim 4, wherein the pressure sensor system comprises:
   a first pressure sensor configured for positioning in fluid communication with the anterior chamber of an eye; and a second pressure sensor located remotely from the first pressure sensor such that the second pressure sensor measures atmospheric pressure, wherein a difference between the readings from the first pressure sensor and the second pressure sensor approximates IOP.

9. The system of claim 8, wherein the second sensor is configured to be disposed in the subconjunctival space of the eye.

10. The system of claim 4, wherein the pressure sensor system comprises:

a first pressure sensor configured for positioning in fluid communication with a drainage site; and a second pressure sensor located remotely from the first pressure sensor such that the second pressure sensor measures atmospheric pressure, wherein a difference between the readings from the first pressure sensor and the second pressure sensor approximates the gauge drainage site pressure.

11. The system of claim 10, wherein the second sensor is configured to be disposed in the subconjunctival space of the eye.

12. An IOP control system for implantation in an eye of a patient, comprising:

a drainage tube configured to convey aqueous humor from an anterior chamber of the eye;

a pressure-driven valve system in fluid communication with the drainage tube, the valve system actuatable in response to pressure differentials acting on the pressure-driven valves and configured to control flow rates of the aqueous humor;

an electrically-driven pump system in fluid communication with the drainage tube and the pressure-driven valve system, the electrically-driven pump system being arranged to selectively control aqueous humor flow rates through the drainage tube and influence the pressure differentials affecting the valve system;

a processor coupled to the electrically-driven pump system;

a pressure sensor system coupled to the processor, the pressure sensor system comprising a first pressure sensor located in fluid communication with the anterior chamber of an eye and a second pressure sensor located at a drainage site; wherein a difference between the readings from the first pressure sensor and the second pressure sensor approximates a pressure differential between the anterior chamber and the drainage site; and a power source;

wherein the processor is configured to control the pump to adjust the rate of aqueous flow through the drainage tube based on sensed pressures.

13. The system of claim 12, wherein the electrically-driven pump system further comprises a memory coupled to the processor, wherein the processor writes values corresponding to sensed pressures to the memory.

14. The system of claim 12, further comprising a data transmission module coupled to the processor.

15. The system of claim 12, wherein the power source is external to the eye and the electrically driven pump system is activated to pump aqueous humor from the anterior chamber when the pump is in the vicinity of the power source; and the electrically driven pump system is deactivated when the pump is not in the vicinity of the power source.

16. An IOP control system for implantation in an eye of a patient, comprising:

a drainage tube configured to convey aqueous humor from an anterior chamber of the eye;

a pressure-driven valve system in fluid communication with the drainage tube, the valve system actuatable in response to pressure differentials acting on the pressure-driven valves and configured to control flow rates of the aqueous humor;

an electrically-driven pump system in fluid communication with the drainage tube and the pressure-driven valve system, the electrically-driven pump system being arranged to selectively control aqueous humor flow rates through the drainage tube and influence the pressure differentials affecting the valve system;

a processor coupled to the electrically-driven pump system;

a pressure sensor system coupled to the processor, the pressure sensor system comprising a first pressure sensor configured for positioning in fluid communication with the anterior chamber of an eye and a second pressure sensor located remotely from the first pressure sensor such that the second pressure sensor measures atmospheric pressure; wherein a difference between the readings from the first pressure sensor and the second pressure sensor approximates IOP; and a power source;

wherein the processor is configured to control the pump to adjust the rate of aqueous flow through the drainage tube based on sensed pressures.

17. The system of claim 16, wherein the second sensor is configured to be disposed in the subconjunctival space of the eye.

18. The system of claim 16, wherein the electrically-driven pump system further comprises a memory coupled to the processor, wherein the processor writes values corresponding to sensed pressures to the memory.

19. The system of claim 16, further comprising a data transmission module coupled to the processor.

20. The system of claim 16, wherein the power source is external to the eye and the electrically driven pump system is activated to pump aqueous humor from the anterior chamber when the pump is in the vicinity of the power source; and the electrically driven pump system is deactivated when the pump is not in the vicinity of the power source.

21. An IOP control system for implantation in an eye of a patient, comprising:

a drainage tube configured to convey aqueous humor from an anterior chamber of the eye;

a pressure-driven valve system in fluid communication with the drainage tube, the valve system actuatable in response to pressure differentials acting on the pressure-driven valves and configured to control flow rates of the aqueous humor;

an electrically-driven pump system in fluid communication with the drainage tube and the pressure-driven valve system, the electrically-driven pump system being arranged to selectively control aqueous humor flow rates through the drainage tube and influence the pressure differentials affecting the valve system;

a processor coupled to the electrically-driven pump system;

a pressure sensor system coupled to the processor, the pressure sensor system comprising a first pressure sensor configured for positioning in fluid communication with a drainage site and a second pressure sensor located remotely from the first pressure sensor such that the second pressure sensor measures atmospheric pressure; wherein a difference between the readings from the first pressure sensor and the second pressure sensor approximates the gauge drainage site pressure; and a power source;
   wherein the processor is configured to control the pump to adjust the rate of aqueous flow through the drainage tube based on sensed pressures.

22. The system of claim 21, wherein the second sensor is configured to be disposed in the subconjunctival space of the eye.

23. The system of claim 21, wherein the electrically-driven pump system further comprises a memory coupled to the processor, wherein the processor writes values corresponding to sensed pressures to the memory.

24. The system of claim 21, further comprising a data transmission module coupled to the processor.

25. The system of claim 21, wherein the power source is external to the eye and the electrically driven pump system is activated to pump aqueous humor from the anterior chamber when the pump is in the vicinity of the power source; and the electrically driven pump system is deactivated when the pump is not in the vicinity of the power source.

* * * * *